United States Patent [19]

Bruzzese et al.

[11] Patent Number: 4,721,728
[45] Date of Patent: Jan. 26, 1988

[54] PANTOTHENYL DERIVATIVES

[75] Inventors: Tiberio Bruzzese; Franco Ottoni; Holger H. Van Den Heuvel, all of Milan, Italy

[73] Assignee: SpA Societa' Prodotti Antibiotici S.p.A., Milan, Italy

[21] Appl. No.: 916,105

[22] Filed: Oct. 7, 1986

[30] Foreign Application Priority Data

Oct. 8, 1985 [IT] Italy ................ 22392 A/85

[51] Int. Cl.$^4$ ............... C07C 101/18; A61K 31/22
[52] U.S. Cl. ................... 514/547; 514/551; 560/170
[58] Field of Search .......... 560/170; 514/547, 551

[56] References Cited

U.S. PATENT DOCUMENTS 3,584,018 6/1971 Casadio ........................ 260/404
4,439,438 3/1984 Cavazza ........................ 560/170

OTHER PUBLICATIONS

Wagner, "Synthetic Organic Chemistry", pp. 479–482, (1953).
American Journal of Physiology, "Renal Functional Effects of 4-Pentenoic Acid an Inhibitor of Fatty Acid Oxidation", pp. 95–101.

*Primary Examiner*—Michael L. Shippen
*Attorney, Agent, or Firm*—Oblon, Fisher, Spivak, McClelland & Maier

[57] ABSTRACT

Compounds of the following general structure (I)

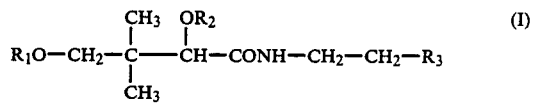

where
$R_1$ stands for an acyl radical of the following structure (II)

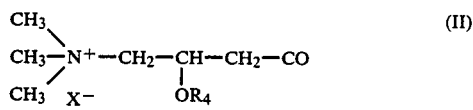

where pl $X^-$ is a halogen atom and $R_4$ is a $C_1$–$C_4$ acyl radical or a hydrogen atom $R_2$ stands for an $R_1$ radical as defined above or for a hydrogen atom $R_3$ stands for a substituted hydroxymethyl $CH_2OR_1$ group, where $R_1$ has the same value as defined above, or for a carboxyl group.

5 Claims, No Drawings

PANTOTHENYL DERIVATIVES

DESCRIPTION

The present invention concerns new pantothenyl derivatives of the following general structure (I)

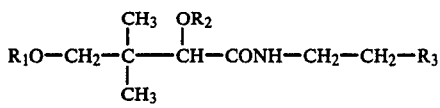

where:

$R_1$ stands for an acyl radical of the following structure (II)

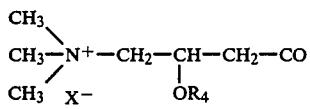

where $X^-$ is a halogen atom and $R_4$ is a $C_1$–$C_4$ acyl radical or a hydrogen atom $R_2$ stands for an $R_1$ radical as defined above or for a hydrogen atom $R_3$ stands for a substituted hydroxymethyl group of —$CH_2OR_1$ formula, in which $R_1$ has the same value as defined above, or for a carboxyl group.

Furthermore, the invention in question covers the chemical method for the preparation of the relevant compounds and their possible use in the clinico-therapeutic field.

It is evident, from the structures shown above, that the compounds of the invention are derived from pantothenol or from pantothenic acid (usually in the D form), in which one or more alcoholic hydroxyls are esterified with either carnitine or with its acyl-derivatives, preferably with acetylcarnitine chloride (chloride of 4-trimethylammonium-3-acetoxy-butyric acid).

Carnitine and the acyl derivatives of it can be utilized in their racemic form or in the "dextro" form, however the "levo" isomer is used to advantage as it is known to be more active in a pharmacologic and biochemical sense and it apparently exhibits lower toxicity.

The possibility of using pantothenol in clinic is already known as the substance is rapidly and completely adsorbed following oral administration, yielding pantothenic acid through biotransformation. The latter is known to carry out a proteoanabolic and lipometabolic action in several metabolic processes, proving thereby useful in all nutritional deficiency conditions, particularly in infancy and very old age, and in hyperlipidemia.

In particular, pantothenic acid is a fundamental constituent of coenzyme A which is directly involved in various phases of energy-producing metabolism, for example as a carrier of free fatty acids, whereby they, in the form of acyl-coenzyme A, can be transferred to the mitochondrial intermembrane space.

Another essential role played by coenzyme A is connected with the reactions of enzyme transfer of acetyl radicals.

Carnitine (and its biologically related acetyl derivatives), is in its levorotory form - a physiologic substance, high concentrations of which are found in tissues and secretions, capable of reactivating important metabolic processes with trophic and anabolic effects: in this sense carnitine is indicated in all cases of malnutrition, anorexia, loss of weight due to any reason.

In particular carnitine is the only carrier of long chain fatty acids, capable of transferring them through the inner mitochondrial membrane in order that they may undergo beta-oxidation with consequent energy production (ATP): the fatty acids present in muscle cell cytoplasm (skeletal muscles and myocardium) and in mitochondrial intermembrane spaces must in fact first undergo activation to acyl-CoA, as described above, then, by further enzymatic transformation, to acyl-carnitine so as to acquire permeability through the mitochondrial inner membrane.

Moreover, carnitine has a favourable influence on sugar metabolism, by stimulating, among others, pyruvic acid oxidative utilization, and thereby it also contributes to increase cell energy availability.

It is therefore indicated in the therapy of both myopathy due to carnitine deficiency in general and in heart pathology (ischemic forms) since the myocardium makes use mostly of fatty acids for energy (beta-oxidation) and this use is strictly dependent upon the quantity of carnitine present.

Acetylcarnitine in particular is essential to the neuronal metabolism and, being able to cross unmodified the blood-brain barrier, is used in clinic to prevent cerebral ageing and other CNS degenerative pathologies.

We have now found that compounds (I) in question present, comparatively to the substances already known, evident advantages from the biochemical-pharmacologic view-point and can find useful application in the therapy of all the pathologies already mentioned. The presence, in the same molecular formula, of both biochemical components (with pantothenic and carnitinic structure) makes it possible for instance, to supply, at the same time, the skeletal and myocardial muscle cells with coenzyme A physiologic precursor to activate the fatty acids with formation of acyl-CoA and their consequent transfer inside the mitochondrial outer membrane, to send sufficient quantities of carnitinic compound to the intermembrane space and therefore to change enzymatically acyl-CoA to acyl-carnitine. The latter therefore will have free access, through the inner membrane, to the mitochondrion in which reversion to acyl-CoA will occur, followed by beta-oxidation and production of energy, in the form of ATP, vital to the cell.

The same synergetic advantages can be likewise observed in other biochemical processes where either pantothenic acid or coenzyme A act concurrently with carnitine.

The products covered by the present invention can be obtained for instance by first preparing the acid chloride of acetylcarnitine by reaction with oxalyl chloride or with thionyl chloride, or by preparing an analogous reactive derivative, and then by proceeding with esterification with pantothenic acid or with pantothenol in suitable molar ratios. Esterification is usually brought about in an inert organic solvent, preferably of the polar and aprotic type, and, at any rate, strictly anhydrous, such as e.g., acetonitrile; at a temperature ranging from 0° to that of the solvent, boiling point, usually at room temperature or somewhat higher (50°–60°), and is completed within less than 24–48 hours.

The new derivatives appear in the form of colourless, crystalline solids, very soluble in water, highly hygroscopic, stable under anhydrous conditions.

As previously mentioned, the products can be extensively used both in the therapy of several pathologic forms and as diabetic substances owing to their eutrophic, anabolic and energizing effects.

For this reason they are used alone or in combination with other drugs, in suitable pharmaceutical forms to be administered by oral, parenteral and other routes, at dosage units of from 50 to 2000 mg.

The pharmaceutical preparations intended for oral use will be in the form of tablets, chewable tablets, capsules and powders, eventually in single dose sachets and effervescent formula, or even syrups, solutions and suspensions in oil, already prepared or to be prepared just before use. The tablets might include excipients such as lactose, saccharose, cellulose etc., and, as usual, lubricating agents such as magnesium stearate and disintegrating agents, e.g., maize starch. The capsules might be of gelatin type, and contain the active ingredient alone or together with suitable diluents. The liquid forms might contain dispersing and suspending agents such as carboxymethyl cellulose, preservatives, etc.

The preparations intended for parenteral administration will be in the form of sterile aqueous solutions or preferably, of lyophilized product to be reconstituted just before use or again of solutions in glycols or suspensions in oleaginous agents.

Some examples are given below to better illustrate the preparation of the compounds in question, without limiting intents whatsoever.

EXAMPLE 1

Acid chloride of L-acetylcarnitine chloride. 2.39 g (0.01 Mol) L-acetylcarnitine chloride is treated with 5 ml oxalyl chloride and the resulting mixture is kept under stirring for 4 hours at room temperature, to complete solution.

The excess oxalyl chloride is evaporated under vacuum and the residue washed 3 times with anhydrous ethyl ether then kept under vacuum till the solvent has completely disappeared. A quantitative yield of the acid chloride of L-acetylcarnitine chloride desired is obtained, that proves substantially pure and is used as an intermediate without further purification.

EXAMPLE 2

Structure (I) compound, in which $R_1=(II)$ (X=Cl, $R_4=CH_3CO$); $R_2=H$; $R_3=COOH$ 11 g (0.05 Mol) of pantothenic acid is dissolved in 500 ml anhydrous acetonitrile then 12.9 g (0.05 Mol) of acid chloride of L-acetylcarnitine chloride dissolved in 150 ml anhydrous acetonitrile is added dropwise to the solution. The reaction mixture is kept for 3 hours under stirring at room temperature, then the solvent is evaporated by distillation under vacuum. The vitreous residue thus obtained is disintegrated and repeatedly washed with ethyl ether, then allowed to dry a long time under vacuum at 60°–80°; 21.6 g (yield 98%) of L-acetylcarnityl-pantothenic acid chloride is obtained in the form of a crystalline colourless solid, to be preserved under anhydrous conditions owing to its high hygroscopic characteristics.

| Analysis for $C_{18}H_{33}ClN_2O_8$ | | (M.W. 440.92) | | |
|---|---|---|---|---|
| % calculated: | C 49.03; | H 7.54; | Cl 8.04; | N 6.35 |
| % found: | C 49.53; | H 7.56; | Cl 8.02; | N 6.34 |

$^1$H-NMR (Sol. $CH_3OD$, ref. TMS) ppm: 0,97 (6H, 2 $CH_3P$), 2.1 (3H, $CH_3CO$ A), 2,5 (2H, $CH_2$-2 P), 2.85 (2H, $CH_2$-2 A), 3.25 (9H, $3CH_3A$), 3.35–4.30 (9H), 5.62 (1H, CH A) (P=pantothenic acid, A=acetylcarnitine)

EXAMPLE 3

Structure (I) compound, in which $R=(II)$ (X=Cl $R_4=CH_3CO$); $R_2=H$; $R_3=CH_2OR_1$ A 2.5 g (0.01 Mol) pantothenol solution in 150 ml anhydrous acetonitrile is added dropwise and under stirring to a 5.16 g (0.02 Mol) acid chloride of L-acetylcarnitine chloride solution in 100 ml of anhydrous acetonitrile. The resulting mixture is reacted for 24 hours at room temperature. Thereafter the solvent is eliminated by distillation under vacuum and with moderate heat, and the vitreous residue is repeatedly treated with ethyl ether, collected by filtration and dried by keeping it several hours at 60°–80° under vacuum. 6.4 g (yield 99%) of the desired diester, di- L-acetylcarnityl-pantothenol chloride, is obtained in the form of a colourless, hygroscopic solid having a crystalline appearance when preserved under anhydrous conditions.

| Analysis for $C_{27}H_{51}Cl_2N_3O_{10}$ | | (M.W. 648.62) | | |
|---|---|---|---|---|
| % calculated: | C 50.00; | H 7.92; | Cl 10.93; | N 6.48 |
| % found: | C 50.10; | H 7.94; | Cl 10.85; | N 6.49 |

$^1$H-NMR (Sol. $CH_3OD$, ref. TMS), ppm: 1.02 (6H, $2CH_3$ P), 2.15 (6H, $2CH_3$ A), 2.9 (4H, $2CH_2$-2 A), 3.3 (20H, $6CH_3$ A, $1CH_2$-2 P), 3.8–4.5 (9H), 5.65 (2H, 2CH A) (P=pantothenol, A=acetylcarnitine)

EXAMPLE 4

Structure (I) compound, in which $R_1=R_2=(II)$ (X=Cl; $R_4=CH_3CO$); $R_3=CH_2O\ R_1$ 2.05 g (0.01 Mol) pantothenol is dissolved in 150 ml anhydrous acetonitrile and added, with stirring, to a solution consisting of 7.74 g (0.03 Mol) of acid chloride of L-acetylcarnitina chloride in 100 ml anhydrous acetonitrile. The reaction mixture is kept for 24 hours at room temperature then for 3 hours at 60° C. Finally the solution is allowed to evaporate under vacuum to obtain a vitreous residue; the residue is repeatedly treated with ethyl ether, then filtered and dried under vacuum for 10 hours at 60°–70° C.: 8.44 g (yield 97%) of tri-L-acetylcarnityl-pantothenol chloride, in the form of a colourless, hygroscopic solid is obtained, m.p.=101°.

| Analysis for $C_{36}H_{67}Cl_3N_4O_{13}$ | | (M.W. 870.30) | | |
|---|---|---|---|---|
| % calculated: | C 49.68; | H 7.76; | Cl 12.22; | N 6.44 |
| % found: | C 49.75; | H 7.80; | Cl 12.19; | N 6.39 |

We claim:

1. Compounds of the following general structure (I)

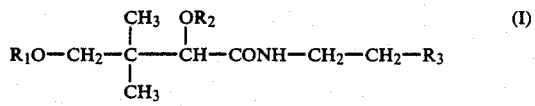

where $R_1$ stands for an acyl radical of the following structure (II)

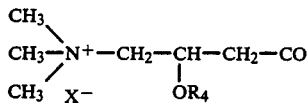 (II)

where $X^-$ is a halogen atom and $R_4$ is an acyl radical $C_1$–$C_4$ or a hydrogen atom $R_2$ for an $R_1$ radical as defined above or for a hydrogen atom $R_3$ stands for a substituted hydroxymethyl $CH_2OR_1$ group, where $R_1$ has the same value as defined above, or for a carboxyl group.

2. A compound according to claim 1, which is L-acetylcarnityl-pantothenic acid chloride.

3. A compound according to claim 1, which is di-L-acetylcarnityl-pantothenol chloride.

4. A compound according to claim 1, which is tri-L-acetylcarnityl-pantothenol chloride.

5. A pharmaceutical formulation exhibiting eutropic, anabolic and energizing effects, for oral or parenteral administration, which comprises, as the active ingredient, 50–2000 mg of a compound of claim 1 and a pharmaceutically acceptable carrier thereof.

* * * * *